United States Patent [19]

Belov et al.

[11] 3,969,429

[45] July 13, 1976

[54] METHOD OF PRODUCING BUTENE-1

[76] Inventors: Gennady Petrovich Belov, p/o Chernogolovka, ulitsa Pervaya, 5, kv. 15; Taimuraz Savelievich Dzhabiev, p/o Chernogolovka, ulitsa Pervaya, 31, kv. 41; Fridrikh Stepanovich Dyachkovsky, p/o Chernogolovka, ulitsa Tretya, 3, kv. 2; Vyacheslav Ivanovich Smirnov, p/o Chernogolovka, ulitsa Tretya, 1, kv. 19; Nelli Dzhavkharovna Karpova, p/o Chernogolovka, ulitsa Pervaya, 29, kv. 100; Khaim-Mordkhe Aronovich Brikenshtein, p/o Chernogolovka, ulitsa Vtoraya, 5, kv. 1; Matrena Petrovna Gerasina, p/o Chernogolovka, ulitsa Pervaya, 2a, kv. 61, all of Moskovskaya oblast, Noginsky raion; Vladimir Evgenievich Kuzmin, ulitsa 50 letiya Oktyabrya, 13/12, kv. 199, Kazan; Petr Evgenievich Matkovsky, p/o Chernogolovka, ulitsa Pervaya, 16, kv. 26, Moskovskaya oblast, Noginsky raion; Ljudmila Nikolaevna Russiyan, p/o Chernogolovka, ulitsa Pervaya, 2a, kv. 41, Moskovskaya oblast, Noginsky raion; Anatoly Dmitrievich Pomogailo, p/o Chernogolovka, ulitsa Pervaya, 33, kv. 15, Moskovskaya oblast, Noginsky raion, all of U.S.S.R.; Nikolai Mikhailovich Chirkov, deceased, late of Moscow, U.S.S.R.; by Mikhail Nikolaevich Chirkov, administrator, ulitsa Vavilova, 55/5, kv. 6, Moscow, U.S.S.R.

[22] Filed: Sept. 8, 1975

[21] Appl. No.: 611,319

Related U.S. Application Data

[60] Continuation of Ser. No. 494,918, Aug. 5, 1974, abandoned, which is a division of Ser. No. 436,809, Jan. 25, 1974, Pat. No. 3,879,485.

[52] U.S. Cl................................. 260/683.15 D
[51] Int. Cl.$^2$............................. C07C 3/10
[58] Field of Search........................ 260/683.15 D

[56] References Cited

UNITED STATES PATENTS

| 2,943,125 | 6/1960 | Ziegler et al.............. | 260/683.15 |
| 3,472,910 | 10/1969 | Favis...................... | 260/683.15 |
| 3,652,705 | 3/1972 | Arakawa.................... | 260/683.15 |
| 3,686,350 | 8/1972 | Ono et al.................. | 260/683.15 |

*Primary Examiner*—C. Davis
*Attorney, Agent, or Firm*—Holman & Stern

[57] ABSTRACT

The present invention relates to a method of producing butene-1.

According to the invention, the method of producing butene-1 resides in dimerizing ethylene in the presence of a complex organometallic catalyst of the formula $(RO)_3TiR' \cdot AlR_2''OR + AlR_2''R'$, where R is an alkyl radical with from 2 to 4 carbon atoms, $R' = R$ or H, $R''$ is the same as R, or a catalyst having the formula $Ti(OR)_4 + AlR_2''R'$ and modifiers such as $(C_5H_5)_2TiCl_2$, oxygen, metaphenylenediamine or N-phenyl-$\beta$-naphthylamine, in the medium of solvents such as n-heptane, n-decane, toluene, diethyl ether, ethyl chloride, vinylbutyl ether, tetrahydrofuran, diphenyl ether, methylphenyl ether and mixtures thereof.

The invention will find application in petrochemical processing.

2 Claims, No Drawings

METHOD OF PRODUCING BUTENE-1

This is a continuation of application Ser. No. 494,918 filed Aug. 5, 1974, now abandoned, which in turn is a division of Ser. No. 436,809 filed Jan. 25, 1974, now U.S. Pat. No. 3,879,485 dated Apr. 22, 1975.

BACKGROUND OF THE INVENTION

The present invention relates to the field of producing unsaturated hydrocarbons, and more particularly to methods of producing butene-1.

Butene-1 can be used in the production of n-butyl alcohol, copolymers of ethylene with butylene, isotactic polybutene, butylene oligomers, as well as in the production of butadiene and other products of petrocnemical processing.

Several methods of producing butene-1 are known in the art: separation of butene-1 from the butane-butylene fraction of cracked gases, dehydration of butyl alcohol, dehydrogenation of butane, and thermal or catalytic dimerization of ethylene.

The process of producing butene-1 by dimerizing ethylene on complex organometallic catalysts has gained wide acceptance. In accordance with the known methods, dimerization of ethylene to butene-1 is carried out at temperatures ranging from 0° to 100°C, preferably from 10° to 40°C, with the pressure of ethylene being either atmospheric or elevated (up to 40 gauge atmospheres), in the medium of organic solvents (heptane, hexane, benzene, toluene, butane, isooctane, or mixtures of these solvents with butene-1).

In the processes of ethylene dimerization, complex catalysts including compounds of nickel, cobalt or titanium are employed.

Catalysts based on nickel or cobalt compounds are noted for their low selectivity.

Reactions of ethylene dimerization conducted with these catalysts give a complex mixture of products consisting of butene-1, cis-trans-butenes-2, hexenes, octenes, etc. The dimerization of ethylene on catalysts consisting of titanium alkoxides and organoaluminium compounds $Ti(OR)_4 + AlR_3'$ or $AlR_2''H$, where R, R', R'' stand for an alkyl, cycloalkyl or aryl hydrocarbon radical in the medium of hydrocarbon solvents, usually results in the formation, along with butene-1, of from 0.5 to 5.0 vol. per cent of butenes-2 and from 1.5 to 8.0 weight per cent of polyethylene.

The dimerization of ethylene on catalysts of this type with an ethylene pressure of from 1 to 10 atm proceeds at a relatively low rate (1 to 2 g/lit per min. with the concentration of $Ti(OR)_4$ of about $5 \cdot 10^{-3}$ mole/lit.). In the course of the process the catalyst rapidly loses its activity, which results in the lowering of its capacity, i.e. in a lower yield of butene-1 in moles per mole of $Ti(OR)_4$.

With a view to increasing the activity and capacity of the catalyst, the process of dimerizing ethylene to butene-1 is recommendably carried out at low temperatures (ranging from 10° to 40°C), this involving considerable difficulties as regards the problem of heat removal.

Low selectivity of the known processes of dimerizing ethylene to butene-1, low yields of the desired product per unit weight of the catalyst, sophisticated and cumbersome process equipment are all factors responsible for the high ultimate cost of butene-1. This is to a considerable extent associated with the fact that the formation of by-products, even in small amounts (2 to 5 weight per cent for the reacted ethylene) aoversely tells on the entire technological process of producing butene-1, since the by-products not only lower the yield of butene-1 and its purity, but also reduce the working time of the process equipment, insofar as solid polymer accumulating in the reactors has to be periodically removed, which can be done only by interrupting the dimerization process and, hence, at the expense of lost time of the equipment operation.

In some cases, for attaining a partial improvement of the process characteristics, it was suggested that the catalyst modifiers be introduced into the reaction mixture in amounts commensurable with the amount of the catalyst components (with the molar ratio modifier/$Ti(OR)_4$ being from 0.01 to 10; and modifier/$AlR_3$ from 0.01 to 1.0).

As such modifiers organic esters of orthophosphoric acid, diphenylamine, phenothiazine, etc. may be used.

The inclusion of these compounds into the composition of the catalyst in amounts of from 0.1 to 1.0 mole per mole of the alkylaluminium taken leads to a certain reduction in the polymer formation; however, the activity and capacity of the catalyst are also essentially reduced in this case.

Different compounds used as modifying additives, even if they belong to the same class of compounds, produce different influence on both the rate of dimerization of ethylene to butene-1 and on the side reactions of the polymerization of ethylene to polyethylene. At present it is hardly possible to establish any definite relationship between the properties of the modifier (its structure, etc.) and the inhibitory effect it produces on the reaction of polymer formation, or its general influence on the process of dimerization of ethylene to butene-1. It is just for this reason that patents teach the application of modifiers of only individual compounds and not of whole classes of compounds.

OBJECTS AND SUMMARY OF THE INVENTION

It is an object of the present invention to increase the catalyst activity.

Another object of the invention is to enhance the selectivity of the process by diminishing the polymerization of ethylene to high-molecular polyethylene, as well as to diminish the rate of or preclude the formation of butenes-2 and higher olefines.

Said objects have been accomplished by the provision of a method of producing butene-1 which resides in the fact that the dimerization of ethylene to butene-1 is carried out, according to the invention, in the presence of a complex organometallic catalyst consisting of titanium alcoholates of the formula $(RO)_3TiR'·AlR_2'\lambda$ 'OR and alkylaluminium of the formula $AlR''_2R'$, where R is an alkyl radical with the number of carbon atoms being from 2 to 4, R' = R or H, and R'' is the same as R, utilized in the medium of hydrocarbon solvents such as n-heptane, n-decane, and toluene.

Titanium alcoholates of the formula $(RO)_3TiR'·AlR''_2OR$ contain ethoxy-, propoxy-, isopropoxy-, butoxy-, isobutoxy-groups linked with titanium and aluminium. As di- and trialkylaluminium of the formula $AlR_2''R'$, triethylaluminium, tributylaluminium, triisobutylaluminium, diisobutylaluminium hydride, tripropylaluminiun, or triisopropylaluminium are utilized. Optimal results are obtained with the catalyst having the formula $(C_4H_9O)_3Ti\ C_2H_5Al(C_2H_5)_2OC_4H_9$.

Depending on the particular conditions, the molar ratio of trialkylaluminium to titanium alcoholate in the catalyst when carrying out dimerization of ethylene to butene-1 is varied within a range of from 1.5 to 100. The concentration of titanium alcoholate in the reaction medium is varied within a range of from $1\cdot 10^{-2}$ to $1\cdot 10^{-5}$ mole/lit. Dimerization is effected at temperatures of 0 to 100°C and at an ethylene pressure of from 1 to 40 atm.

Said objects are also accomplished by the provision of a method of producing butene-1, wherein, according to the invention, dimerization of ethylene to butene-1 is carried out in the presence of a complex organometallic catalyst consisting of titanium alcoholates of the formula $Ti(OR)_4$ and alkylaluminium of the formula $AlR_2''R'$, where R is an alkyl radical with the number of carbon atoms being from 2 to 4, $R' = R$ or H, $R''$ is the same as R, in the medium of hydrocarbon solvents such as n-heptane, -decane, toluene, with said catalyst being modified by additives selected from the group consisting of dicyclopentadienyltitanium dichloride, oxygen, metaphenylenediamine, N-phenyl-$\beta$-naphthylamine.

The process of dimerization of ethylene to butene-1 by the method of the invention can also be effected in the presence of amines such as diethylamine, diisopropylamine, triethylamine, though the yield of butene-1 in this case materially decreases in spite of the fact that the selectivity of the catalyst is enhanced.

The above-mentioned objects are also accomplished by the provision of a method of producing butene-1, residing in the fact that the dimerization of ethylene to butene-1 is carried out in the presence of a complex organometallic catalyst consisting of titanium alcoholates of the formula $Ti(OR)_4$ and an alkylaluminium of the formula $AlR_2''R'$, where R is an alkyl radical with from 2 to 4 carbon atoms, $R' = R$ or H, and $R''$ is the same as R, taken in the medium of solvents such as ethyl chloride, ethers selected from the group consisting of diethyl, vinylbutyl, diphenyl ethers, tetrahydrofuran, a mixture of heptane with ethyl chloride, a mixture of diethyl ether with butene-1, and a mixture of diethyl ether with ethyl chloride.

The dimerization of ethylene to butene-1 also takes place in the presence of the above-mentioned catalysts when dimethyl ether, anisole, -phenetole, methyl-butyl ether are used as solvents.

Among the above-cited solvents low-boiling ones are preferable for carrying out the dimerization of ethylene to butene-1 (e.g. ethyl chloride, diethyl ether), whose boiling point substantially differs from that of butene-1. The use of these solvents facilitates heat removal, isolation of butene-1 and the rectification of the solvent.

According to the invention, modifying additives, viz., dicyclopentadienyltitanium dichloride, oxygen, metaphenylenediamine, N-phenyl-$\beta$-naphthylamine, are taken in amounts of from 0.05 to 2.0 mole per mole of alkylaluminium. The use of dicyclopentadienyltitanium dichloride does not change the phase state of the catalyst, since dicyclopentadienyltitanium dichloride, as well as the other two components of the catalyst, $Ti(OR)_4$ and $AlR_2''R'$, is soluble in the reaction medium and does not form a heterogeneous phase.

The modification of the catalyst $Ti(OR)_4 + AlR_2''R'$ by additions of oxygen allows a 10 to 20 per cent increase in the yield of butene-1 with a simultaneous enhancement of the process selectivity.

The quantity of oxygen in the reaction vessel is varied within 0.2:1 to 2:1 with regard to the quantity of alkylaluminium present therein.

The yield of butene-1 in the presence of oxygen reaches 342 g per gram of $Ti(OC_4H_9)_4$, whereas the best result in the absence of oxygen is 312 g per gram of $Ti(OR)_4$. The content of higher olefines and polyethylene in the reaction products diminishes from 5.3 to 1.7 weight per cent.

Modifiers are introduced into the reaction vessel either prior to feeding the catalyst, or in the course of the dimerization process. Best results are obtained with N-phenyl-$\beta$-naphthylamine and metaphenylenediamine. The application of these compounds as additives wholly suppresses the reaction of polymer formation.

In the herein-proposed method of producing butene-1 on the catalyst $(RO)_3TiR'\cdot AlR_2''OR$ the yield of butene-1 per unit weight of the catalyst, as compared with the known method of producing butene-1 (245.6 g per gram of the catalyst), increases by about 25 weight per cent and reaches 312 g per gram of the catalyst. Moreover, while in the known method the quantity of the by-products makes from 8.5 to 25.5 weight per cent, while in the present method the respective figure does not exceed 5.3 weight per cent. The replacement of the earlier employed titanium alcoholate $(RO)_4Ti$ by the complex alcoholate $(RO)_3TiR'\cdot AlR_2''OR$ allows for an increase in the initial rate of dimerization and an approximately 1.5 times better yield of butene-1 (from 31.1 g/lit. per hour to 45.7 g/lit. per hour).

The modification of the catalyst $Ti(OR)_4 + AlR_2''R'$ by the above-mentioned additives allows for a 10 to 20 per cent increase in the yield of butene-1 with a simultaneous enhancement of the process selectivity.

The employment of such heteroatom-containing solvents as the reaction medium such as ethers (diethyl, dimethyl, dibutyl, methylbutyl, diphenyl, divinyl, diallyl ether, tetrahydrofuran) allows for an almost ten-fold increase in the dimerization rate, a raise in the yield of butene-1 to from 2–3 kg per gram of titanium alcoholate, and for the complete elimination of the formation of butenes-2, higher olefines and polyethylene.

When the method of the invention is effected in the medium of oxygen-containing solvents, the concentration of the catalyst can be varied from $1\cdot 10^{-6}$ to $1\cdot 10^{-1}$ mole/lit. The molar ratio of the catalyst components can also be varied within a wide range (Al/Ti = 2.0 – 2000). In case of low molar ratios (Al/Ti less than 2.0) dimerization does not take place. When ethylene the dimerization is carried out in the medium of heteroatom-containing solvents as the main catalyst component, either complex titanium alcoholates $(RO)_3TiR'\cdot AlR_2''OR$, or individual titaium alcoholates $(OR)_4Ti$ can be used.

Bringing down the catalyst concentration to $1\cdot 10^{-4} - 1\cdot 10^{-5}$ mole/lit., with all other things being equal, allows for a sharp increase in the catalyst efficiency (up to 20000 moles of butene-1 per mole of $Ti(OR)_4$).

It has been established that the catalyst in diethyl ether and tetrahydrofuran at temperatures of from 20° to 40°C does not lose its activity for a period of 48 hours. At low temperatures (from –40 to +20°C) the dimerization of ethylene starts after a long induction period, this period as such being conditioned by the reactions of the formation of active centres in the system $Ti(OR)_4 - AlR_3'$. When ethylene is dimerized on $(RO)_3TiR'.AlR'2''OR - AlR_3$ under otherwise equal conditions, the induction period characterized by the absence of the ethylene dimerization reaction either diminishes or disappears.

Within the temperature range of +50° to 100°C the induction period is practically absent and dimerization starts immediately after blending the catalyst components. For the best results as to the dimerization rates, the yield of butene-1 and the catalyst selectivity have been obtained when dimerizing ethylene in the medium of diethyl ether, at temperatures ranging from +40° to + 80°C, a ethylene pressures ranging from 2 to 12 atm and at Al/Ti molar ratios of from 10 to 50. Under said conditions the rate of dimerization of ethylene to butene-1 with the concentration of $Ti(OR)_4$ being 0.55 mmole/lit. reaches 10 g/lit, per minute, with the yield of butene-1 being 2500 g per gram of $Ti(OR)_4$, and by-products, i.e. polyethylene, butenes-2 and higher olefines are absent altogether.

Similar results have been obtained when using as the reaction medium, mixtures of heteroatom-organic compounds with hydrocarbons or their chlorine-containing derivatives, such as diethyl ether + butene-1; diethyl ether + n-heptane, diethyl ether + ethyl chloride, and tetrahydrofuran + ethyl chloride, etc.

DETAILED DESCRIPTION OF THE INVENTION

Given hereinbelow is a description of the preferred embodiment of the method of the invention.

The dimerization of ethylene to butene-1 (unless otherwise specified) was carried out in a steel temperature-controlled reactor equipped with a stirrer provided with a screened drive. With the aid of said stirrer the reaction mass was intensively stirred (at a speed of about 1500 r.p.m.). Before the experiments the apparatus was heated to 60°C and the air was evacuated therefrom by means of a vacuum pump to a pressure below $10^{-2}$ mm Hg for 1 hour, after which the apparatus was blown with ethylene. This being done, 0.2 lit. of diethyl ether was fed into the reactor at a preset temperature, namely, +40°C, which was established therein, and ethylene was fed into the reactor in such an amount as to ensure the required ethylene pressure, namely, 8.0 atm. Then 0.1937 g of an alcoholate $(C_4H_9O)_3TiC_2H_5.Al(C_2H_5)_2OC_4H_9$ and 3.05 g of triethylaluminium (Al/Ti = 49.5) were introduced into the reactor. The dimerization of ethylene to butene-1, which commenced immediately upon introducing of 3.05 g of triethylaluminium, was carried out under constant pressure, this being attained by continuously feeding ethylene into the reactor from a gas bottle. The process was run for 250 minutes until the reactor was completely filled with butene-1. The reaction of ethylene dimerizing to butene-1 was interrupted by adding 20 ml of ethyl alcohol into the reactor. The resultant butene-1 together with the solvent and catalyst were discharged from the reactor through its bottom valve into a rectification still column. 445 g of butene-1 were produced. The average rate of dimerization of ethylene to butene-1 was 8.52 g/lit. per minute, the yield was 2330 g of butene-1 per gram of $Ti(OC_4H_9)_4$, this corresponding to 14150 mole of butene-1 per mole of $Ti(OC_4H_9)_4$. Chromatographic analysis of the reaction products showed an absence of polyethylene, butenes-2 and higher olefines.

Other features and advantages of the herein-proposed method of producing butene-1 will become apparent from the following detailed description of specific examples illustrating the embodiments thereof.

EXAMPLE 1

A 250 ml capacity steel reactor equipped with a propeller stirrer (1400 r.p.m) is charged with 100 ml of heptane, and $3.5·10^{-4}$ mole of $(C_4H_9O)_3TiC_2H_5.Al(C_2H_5)_2(OC_4H_9)$, whereupon the reactor is heated to 40°C and then filled with ethylene to a pressure of 10 atm, whereupon $5·10^{-3}$ mole of $Al(C_2H_5)_3$ is injected thereinto it.

The dimerization reaction is run for two hours at the above-stated constant pressure of ethylene and then terminated by introducing 10 ml of ethyl alcohol into the reactor. The content of higher olefines is determined chromatographically, with the polymer being wasted with ethyl alcohol and dried to a constant weight.

49.5 g of butene-1, 1.5 g of higher olefines and 1.3 g of the polymer are obtained. The yield of butene-1 is 312 g per gram of the complex titanium alcoholate. The yield of the by-products is 5.3 weight per cent.

EXAMPLE 2

By following the procedure outlined in Example 1 the dimerization of ethylene to butene-1 is carried out in the medium of n-decane, at a temperature of 20°C, and an ethylene pressure of 2.7 atm, for a period of 96 min, the resulting product contains 18 g of butene-1. The content of butene-1, higher olefines and the polymer in the resulting product is 97.5, 1.9 and 0.6 weight per cent respectively.

EXAMPLE 3

Under the conditions of Example 2, $(C_2H_5O)_3TiC_2H_5.Al(C_2H_5)_2(OC_2H_5)$ is used as titanium alcoholate. In 120 minutes a product is obtained containing 22 g of butene-1. The content of butene-1, higher olefines and the polymer in the product is 96.3, 2.8 and 0.9 weight per cent respectively.

EXAMPLE 4

A glass reactor having a capacity of 50 ml and equipped with a magnetic stirrer is charged with 20 ml of n-heptane, and $0.1·10^{-3}$ mole of $(C_4H_9O)_3TiC_2H_5.Al(C_2H_5)_2(OC_4H_9)$, and an ethylene pressure of 0.55 atm being established therein at a temperature of 22°C, $0.38·10^{-3}$ mole of $Al(C_2H_5)_3$ is then added.

The initial dimerization rate is 45.7 g/lit. per hour.

EXAMPLE 5

Under the conditions of Example 4, $Ti(OC_4H_9)_4$ is used.

The initial rate of ethylene dimerization is 31.1 g/lit. per hour.

EXAMPLE 6

Under the conditions similar to those described in Example 1 the dimerization of ethylene is carried out at a temperature of 20°C, and an ethylene pressure of 1.7 atm, in the medium of ethyl chloride. As the titanium alcoholate $(C_6H_5CH_2O)_3TiC_2H_5.Al(C_2H_5)_2.(OCH_2C_6H_5)$ and $Al(iso-C_4H_9)_2H$ is used. After a period of 120 minutes a product is obtained containing 12.8 g of butene-1, 0.2 g of higher olefines and 0.3 g of a polymer, this corresponding to 96.25, 1.5 and 2.25 weight per cent respectively.

EXAMPLE 7

Under the conditions of Example 6, Ti(OCH$_2$C$_6$H$_5$)$_4$ is used. 8 g of a product are obtained, wherein butene-1 makes 88 weight per cent thereof, and the higher olefines and the polymer, 12 weight per cent.

EXAMPLE 8

A steel reactor having a capacity of 250 ml is charged with 89 ml of ethyl chloride, $5 \cdot 10^{-4}$ mole of Ti(OC$_4$H$_9$)$_4$ and $2.5 \cdot 10^{-5}$ mole of (C$_5$H$_5$)$_2$TiCl$_2$.

A pressure of 3 atm is established in the reactor and $5 \cdot 10^{-3}$ mole of Al(C$_2$H$_5$)$_3$ is introduced thereinto at a temperature of 30°C. The reaction is run for 90 min. and gives 44.2 g of butene-1, and 0.8 g of higher olefines and polymer. The yield of the butene-1 is 260 g per gram of Ti(OC$_4$H$_9$)$_4$; that of the higher olefines and the polyethylene is 1.78 weight per cent.

EXAMPLE 9

Under the conditions similar to those of Example 8 the amount of (C$_5$H$_5$)$_2$TiCr$_2$ charged into the reactor is $1.2 \cdot 10^{-4}$ mole. After a period of 90 min. 47 g of butene-1 and 0.9 g of higher olefines and polymer are obtained. The yield of butene-1 is 276 g per gram of Ti(OC$_4$H$_9$)$_4$, with the yield of the by-products making 1.87 weight per cent.

EXAMPLE 10

Under the conditions of Example 8 the amount of (C$_5$H$_5$)$_2$TiCl$_2$ charged into the reactor is $5 \cdot 10^{-4}$ mole. The reaction lasting for 90 min. which gives 32 g of butene-1 and 0.7 g of higher olefines and polymer. The yield of butene-1 is 187 g per gram of Ti(OC$_4$H$_9$)$_4$, with that of by-products being 2.14 weight per cent.

EXAMPLE 11

A steel reactor having a capacity of 250 ml is charged with 100 ml of ethyl chloride and ethylene is fed into the reactor at a temperature of 20°C to a pressure of 3 atm. Then $5 \cdot 10^{-4}$ mole of Ti(OC$_4$H$_9$)$_4$, $5 \cdot 10^{-3}$ mole of Al(C$_2$H$_5$)$_3$ and $5 \cdot 10^{-3}$ mole of oxygen are introduced into the reactor. The reaction is run for 240 minutes and yields 58 g of butene-1, 0.46 g of higher olefines and 0.53 g of polyethylene. The yield of butene-1 is 342 g per gram of Ti(OC$_4$H$_9$)$_4$, and the total yield of by-products is 1.7 weight per cent.

EXAMPLE 12

A reaction similar to that of Example 11 is conducted and charged with 100 ml of n-heptane, $2 \cdot 10^{-4}$ mole of Ti(OC$_4$H$_9$)$_4$, $2 \cdot 10^{-3}$ mole of Al(C$_2$H$_5$)$_3$ and $1 \cdot 10^{-3}$ mole of oxygen. The reaction run for 186 min. gives 20.4 g of butene-1, 0.35 g of higher olefines and 0.42 g of polymer. The yield of butene-1 is 234 g per gram of Ti(OC$_4$H$_9$)$_4$, and the total yield of by-products is 3.7 weight per cent.

EXAMPLE 13

A reaction similar to that of Example 11 is conducted with 100 ml of toluene, $5 \cdot 10^{-4}$ mole of Ti(OC$_4$H$_9$)$_4$, $5 \cdot 10^{-3}$ mole of Al(C$_2$H$_5$)$_3$ and $10 \cdot 10^{-3}$ mole of oxygen. The result is 21 g of butene-1 and 2.9 weight per cent of by-products.

EXAMPLE 14

The conditions are the same as in Example 11, except that the amount of oxygen charged into the reactor is $1.0 \cdot 10^{-3}$ mole and the ethylene pressure is established at 6.9 atm. The reaction is run for 100 min. which gives 31 g of butene-1. The content of higher olefines and polyethylene in the reaction products is 1.5 weight per cent.

EXAMPLE 15

Under the conditions of Example 13 no oxygen is added into the reactor. The reaction time is 240 min., with the result of 33.4 g of butene-1 and 1.25 g of higher olefines and polyethylene being obtained. The yield of butene-1 is 197 g per gram of Ti(OC$_4$H$_9$)$_4$, or 96.4 weight per cent.

EXAMPLE 16

A steel reactor of a 400 ml capacity is charged with 100 ml of n-heptane, 0.27 g of metaphenylenediamine, $5 \cdot 10^{-4}$ mole of Ti(OC$_4$H$_9$)$_4$ and $5 \cdot 10^{-3}$ mole of Al(C$_2$H$_5$)$_3$. The molar ratio of Al(C$_2$H$_5$)$_3$ to metaphenylenediamine is 2:1. At an ethylene pressure of 3 atm and at a temperature of 20°C, maintained for a period of 280 min. 44 g of butene-1 and 0.6 g of higher olefines are obtained. No polymer is detected in the reaction products. The yield of butene-1 is 260 g per gram of Ti(OC$_4$H$_9$)$_4$, or 98.55 weight per cent.

EXAMPLE 17

Under the conditions of Example 16 the molar ratio of Al(C$_2$H$_5$)$_3$ to metaphenylenediamine is 1:1. After 90 min. 7 g of butene-1 and 0.1 g of higher olefines are obtained. Polyethylene is not detected in the reaction products.

EXAMPLE 18

Under the conditions of Example 16, the molar ratio of Al(C$_2$H$_5$)$_3$ to metaphenylenediamine is 10:1. After 90 min. the reaction yields 9.5 g of butene-1, 0.18 g of higher olefines and traces of polymer.

EXAMPLE 19

Under the conditions of Example 16, 0.525 g of N-phenyl-$\beta$-naphthylamine is employed. After 90 min. 17 g of butene-1 and 0.22 g of the higher olefines are obtained. The polymer is absent.

EXAMPLE 20

Under conditions similar to Example 17, diisopropylamine is used. The result is 16.8 g of butene-1, 0.25 g of higher olefines, and traces of polymer.

EXAMPLE 21

Under the conditions of Example 17, diethylamine is employed. 16.3 g of butene-1, 0.2 g of higher olefines, and traces of polymer are obtained.

EXAMPLE 22

Under the conditions of Example 17, $1 \cdot 10^{-3}$ mole of triethylamine is employed. With the molar ratio of Al(C$_2$H$_5$)$_3$ to N(C$_2$H$_5$)$_3$ being 5.1, 11 g of butene-1, 0.1 g of higher olefines, and 0.06 g of polymer are obtained.

EXAMPLE 23

A steel reactor having a capacity of 250 ml is charged with 84 ml of ethyl chloride, 16 ml of heptane, $5 \cdot 10^{-4}$ mole of Ti(OC$_4$H$_9$)$_3$C$_2$H$_5$·Al(C$_2$H$_5$)$_2$(OC$_4$H$_9$) and $9 \cdot 10^{-3}$ mole of Al(C$_2$H$_5$)$_3$. With a constant pressure of ethylene being maintained at 5.7 atm and at a temperature of 20°C, 23 g of butene-1 and 0.1 g of solid polyethylene are obtained after 97 min. The content of butane in the gaseous phase is about 1 per cent.

EXAMPLE 24

Under the conditions of Example 23 toluene is used as the solvent and the ethylene pressure is 6.9 atm. After 96 min. 17.5 g of butene-1 and 0.3 g of polyethylene are obtained. The content of butene-1 in the gas mixture is 97 per cent, that of butane and higher olefines is 3 per cent.

EXAMPLE 25

A steel reactor having a capacity of 250 ml is charged with 87.5 ml of ethyl chloride, $5 \cdot 10^{-4}$ mole of Ti(OC$_4$H$_9$)$_4$, $5 \cdot 10^{-4}$ mole of Al(C$_2$H$_5$)$_3$. With an ethylene pressure of 6.9 atm, 23 g of butene-1 are obtained after 97 min. The content of butene-1 in the gas mixture is 98.5 per cent, and that of butane and the higher olefines is 1.5 per cent.

EXAMPLE 26

A steel reactor having a capacity of 250 ml is charged with 90 ml of ethyl chloride, 10 ml of n-heptane, $5 \cdot 10^{-4}$ mole of Ti(iso-C$_3$H$_7$O)$_4$, $5 \cdot 10^{-3}$ mole of Al(C$_2$H$_5$)$_3$. At 20°C and at an ethylene pressure of 2.7 atm for 70 min. 4.55 g of butene-1 are obtained, this corresponding to 98.5 weight per cent.

EXAMPLE 27

A steel reactor having a capacity of 1000 ml is charged with 200 ml of diethyl ether, 0.6 g of Ti(OC$_4$H$_9$)$_4$ and 0.2 g of Al(C$_2$H$_5$)$_3$. 30 minutes later another 1.8 g of Al(C$_2$H$_5$)$_3$ is added into the reactor. The ethylene pressure established in the reactor is 8.0 atm. After 4 hours at 40°C 151 g of butene-1 are obtained. The average dimerization rate is 5.25 g/lit. per minute, or 385 moles of butene-1 per mole of Ti(OC$_4$H$_9$)$_4$ per hour. With the experiment being continued after 16 hours, another 175 g of butene-1 are obtained after 110 minutes under the same conditions, with the dimerization rate being 7.9 g/lit. per minute. The total yield of butene-1 is 547 g per gram of Ti(OC$_4$H$_9$)$_4$, which makes 3320 moles of butene-1 per mole of Ti(OC$_4$H$_9$)$_4$. Butenes-2, higher olefines and polyethylene are not detected in the reaction products.

EXAMPLE 28

A steel reactor having a capacity of 1000 ml is charged with 220 ml of diethyl ether, 0.375 g of tetrabutoxytitanium and 1.245 g of triethylaluminium (Al/Ti = 10.0). At a temperature of +60°C and at an ethylene pressure of 8.0 atm, after 6.5 hours 545 g of butene-1 are obtained. The yield of butene-1 is 1500 g per gram of Ti(OC$_4$H$_9$)$_4$, this corresponding to 8850 moles of butene-1 per mole of Ti(OC$_4$H$_9$)$_4$. Cis- and transbutenes-2, higher olefines and polyethylene are absent in the reaction products.

EXAMPLE 29

A steel reactor is charged with 200 ml of diethyl ether, 0.1875 g of tetrabutoxytitanium and triethylaluminium in two portions (0.2 g + 2.26 g) at an interval of 30 minutes (Al/Ti = 39.2). At 60°C and at an ethylene pressure of 16.0 atm, 364 g of butene-1 are obtained after 314 minutes (the reaction having been stopped 4 hours after the commencement and then the experiment continued after an interval of 16 hours). The average dimerization rate is 5.8 g/lit. per minute, the yield is 11800 moles of butene-1 per mole of Ti-OC$_4$H$_9$)$_4$, or 1940 g of butene-1 per gram of Ti-(OC$_4$H$_9$)$_4$. No by-products are detected.

EXAMPLE 30

A reactor is charged with 200 ml of diethyl ether, 0.1875 g of Ti(OC$_4$H$_9$)$_4$ and 3.11 g of triethylaluminium (Al/Ti = 49.6). At 40°C and an ethylene pressure of 8.0 atm, after 250 minutes 435 g of butene-1 are obtained. The average dimerization rate is 8.5 g/lit. per minute, the yield is 2320 g per gram of Ti-(OC$_4$H$_9$)$_4$, which corresponds to 14100 moles of butene-1 per mole of Ti(OC$_4$H$_9$)$_4$. The process selectivity is 100 per cent.

EXAMPLE 31

A reactor is charged with 200 ml of vinylbutyl ether, 5.2 g of tetrabutoxytitanium and 17.2 g of Al(C$_2$H$_5$)$_3$. After 6 hours at a temperature of 60°C and an ethylene pressure of 12 atm, 40 g of butene-1 are obtained.

EXAMPLE 32

A reactor is charged with 200 ml of tetrahydrofuran, 0.36 g of tetrabutoxytitanium and 5 g of triethylaluminium. At a temperature of 60°C and an ethylene pressure of 12 atm 32 g of butene-1 are obtained after 10 hours.

EXAMPLE 33

A reactor is charged with 50 ml of butene-1, 40 ml of diethyl ether, 0.17 g of tetrabutoxytitanium and 0.57 g of triethylaluminium. At a temperature of 60°C and an ethylene pressure of 8.0 atm, 95 g of butene-1 are obtained after 6.5 hours. After 16 hours the experiment is continued at a pressure of 16 atm. After 1 hour at a temperature of 60°C another 25 g of butene-1 are obtained. Cis-, trans-butenes-2, oligomers of ethylene and polyethylene are not detected in the reaction products. The yield of butane-1 is 900 g per gram of Ti(OC$_4$H$_9$)$_4$.

EXAMPLE 34

A reactor is charged with 50 ml of diethyl ether, 50 ml of ethyl chloride, 0.17 g of tetrabutoxytitanium and 1.14 g of triethylaluminium. At a temperature of 60°C and an ethylene pressure of 8.0 atm, 6.0 g of butene-1 are obtained after 60 minutes. Selectivity is 100%.

EXAMPLE 35

A reactor is charged with 200 ml of diethyl ether, 0.204 g of tetrabutoxytitanium and 10 g of diisobutylaluminium hydride. At a temperature of 60°C and an ethylene pressure of 7.3 atm, 141 g of butene-1 are obtained after 109 minutes. Cis-, trans-butenes-2, ethylene oligomers and polyethylene are not detected in the reaction products.

EXAMPLE 36

A reactor is charged with 200 ml of diphenyl ether, 0.5 g of tetrabutoxytitanium, and 3.2 g of triethylaluminium (Al/Ti = 20). At a temperature of +60°C and an ethylene pressure of 5.0 atm, 150 g of butene-1 are obtained after 52.5 minutes. The yield is 300 g of butene-1 per gram of tetrabutoxytitanium, or 1910 moles of butene-1 per mole of $Ti(OC_4H_9)_4$. Selectivity is 100 per cent.

EXAMPLE 37

A reactor is charged with 200 ml of methylphenyl ether (aniscle), 0.1875 g of tetrabutoxytitanium and 2.55 g of triethylaluminium (Al/Ti = 40). At a temperature of 40°C and an ethylene pressure of 8.0 atm, 307.5 g of butene-1 are obtained after 240 minutes. The yield of butene-1 is 1640 g per gram of $Ti(OC_4H_9)_4$. Selectivity is 100 per cent.

What is claimed is:

1. A method of producing butene-metaphenylenediamine, comprising dimerizing ethylene in the presence of a complex organometallic catalyst consisting of titanium alcoholates of the formula $Ti(OR)_4$ and alkylaluminium of the formula $AlR_2''R'$, where R is an alkyl radical having from 2 to 4 carbon atoms, R' is either the same as R or is H, R'' is the same as R', with said catalyst being modified by an additive for decreasing formation of by-products selected from the group consisting of dicyclopentadienyltitanium dichloride, oxygen, methaphenylenediamine, and N-phenyl-β-naphthylamine, and in the medium of a hydrocarbon solvent selected from the group consisting of n-heptane, n-decane, and toluene.

2. The method as claimed in claim 1, wherein dicyclopentadienyltitanium dichloride, oxygen, metaphenylenediamine, N-phenyl-β-naphthylamine are used as additives in amounts of from 0.05 to 2.0 mole per mole of said alkylaluminium.

* * * * *